United States Patent
Gibb et al.

(10) Patent No.: US 6,937,951 B2
(45) Date of Patent: Aug. 30, 2005

(54) ADAPTIVE PROXIMITY SENSING

(75) Inventors: William J. Gibb, San Anselmo, CA (US); Michael Smidebush, Concord, CA (US); Francisco Miguel Hernandez-Guerra, Concord, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 9 days.

(21) Appl. No.: 10/453,958

(22) Filed: Jun. 3, 2003

(65) Prior Publication Data

US 2004/0249584 A1 Dec. 9, 2004

(51) Int. Cl.$^7$ .............................................. G06F 19/00
(52) U.S. Cl. ........................................ 702/75; 324/674
(58) Field of Search ............................ 702/75, 76, 94, 702/128, 150, 189; 361/179, 182; 324/658, 667

(56) References Cited

U.S. PATENT DOCUMENTS

| | | |
|---|---|---|
| 5,166,679 A | 11/1992 | Vranish et al. |
| 5,373,245 A | 12/1994 | Vranish |
| 5,442,347 A | 8/1995 | Vranish |
| 5,515,001 A | 5/1996 | Vranish |
| 5,521,515 A | 5/1996 | Campbell |
| 6,408,051 B2 | 6/2002 | Habraken et al. ........... 378/117 |
| 6,593,755 B1 | 7/2003 | Rosengren |
| 2003/0076118 A1 | 4/2003 | Adams et al. |

FOREIGN PATENT DOCUMENTS

EP      0 518 836 A1      12/1992

*Primary Examiner*—Edward Raymond

(57) ABSTRACT

Some embodiments provide a sensor element, a shield element capacitively coupled to the sensor element and to ground, a coupling circuit to receive an input signal, and to electrically couple the received input signal to the sensor element and to the shield element, an output circuit to generate an output signal, the output signal based on a capacitance between the sensor element and an object, and a classifier to determine a material based on the output signal, and to transmit a material signal to the output circuit based on the determined material, wherein the output circuit is adjustable based on the material signal.

18 Claims, 7 Drawing Sheets

ADAPTIVE PROXIMITY SENSING

BACKGROUND

1. Field

The present invention relates generally to object detection, and more particularly to systems for sensing a composition and/or a location of an object.

2. Description

Non-contact sensors may be used to determine a distance between two objects. Such sensors are sometimes useful for anticipating and/or avoiding collisions. In one approach, a non-contact sensor is mounted on a first object and determines a distance between the first object and a second object. If the second object is less than a predetermined distance from the first object, additional system elements may output a warning or execute an avoidance maneuver.

Non-contact sensors may operate based on inductance or capacitance. Inductive sensors may be particularly suitable for detecting metallic objects, while capacitive sensors may be more suitable for other types of objects, including biological materials. A typical capacitive sensing system generates an electric field between a sensor and an object of interest and measures a capacitance between the sensor and the object based on a magnitude of the electric field. The sensor then determines a distance to the object based on the measured capacitance. A significant portion of the electric field flows from the sensor to ground rather than to the object, thereby decreasing the accuracy of the determined distance.

U.S. Pat. No. 5,166,679, entitled "Driven Shielding Capacitive Proximity Sensor", describes a particular type of capacitive sensor known as a "capaciflector". The capaciflector attempts to provide greater sensitivity than traditional capacitive sensors by reducing a portion of the generated electric field that flows between a sensor element and ground.

FIG. 1 illustrates the operation of a capaciflector according to the above-mentioned patent. As shown, capaciflector 10 is positioned to sense object 20. Capaciflector 10 includes sensor element 12, dielectric 14, shield element 16 and dielectric 18. Sensor element 12 and shield element 16 may be composed of dissimilar materials, and dielectrics 14 and 18 may also be composed of dissimilar materials.

Capaciflector 10 is mounted to grounded structure 30. The elements of capaciflector 10 are not necessarily drawn to scale, and may comprise layers of extremely small thickness in comparison to dimensions of structure 30. In this regard, a distance between capaciflector 10 and object 20 may be substantially equal to a distance between structure 30 and object 20.

During some examples of operation, sensor element 12 and shield element 16 are both electrically coupled to an input signal. Accordingly, substantially no electric field is generated between sensor element 12 and shield element 16. Electric field lines therefore emanate primarily from sensor element 12 toward object 20, with only some, if any, field lines flowing from sensor element 12 to structure 30. The resulting range and sensitivity of capaciflector 10 may be substantially greater than that of other capacitive sensors.

As described above, the distance between a capacitive sensor and an object is determined based on the capacitance therebetween. However, for a given distance and input signal, the capacitance may vary based on a material of which the object is composed. The accuracy of current proximity sensors therefore depends on the material of the object to be sensed.

In view of the foregoing, a substantially material-independent system is desired for accurately and efficiently determining a distance to an object.

SUMMARY

To address the foregoing, some embodiments provide a sensor element, a shield element capacitively coupled to the sensor element and to ground, and a coupling circuit to receive an input signal, to electrically couple the received input signal to the sensor element and to the shield element, and to generate an output signal, the output signal based on a capacitance between the sensor element and an object. These embodiments also provide a classifier to determine a material based on the output signal and to output a material-based signal, the material-based signal based on the determined material, and a proximity evaluator to detect the object based on the output signal and on the material-based signal.

Some embodiments may involve reception of a first input signal, the first input signal comprising a broad frequency-spectrum signal, generation of a first output signal, the first output signal based on the first input signal and on a material of an object, and determination of the material of the object based on the first output signal. Such embodiments further include generation of a material-based signal based on the material, reception of a second input signal, generation of a second output signal, the second output signal based on the second input signal, and detection of the object based on the second output signal and on the material-based signal.

Embodiments may provide a sensor element, a shield element capacitively coupled to the sensor element and to ground, a coupling circuit to receive an input signal, to electrically couple the received input signal to the sensor element and to the shield element, and to generate an output signal, the output signal based on a capacitance between the sensor element and an object, and a classifier to determine a material based on the output signal and to transmit a material-based signal to the coupling circuit, the material-based signal based on the determined material. The coupling circuit may be adjustable based on the material-based signal.

In further aspects, provided are reception of a first input signal, the first input signal comprising a broad frequency-spectrum signal, generation of a first output signal using a first configuration of a system, the first output signal based on the first input signal and on a material of an object, determination of the material of the object based on the first output signal, change of the first configuration to a second configuration based on the determined material, reception of a second input signal, generation of a second output signal using the second configuration of the system, the second output signal based on the second input signal, and detection of the object based on the second output signal.

The claimed invention is not limited to the disclosed embodiments, however, as those of ordinary skill in the art can readily adapt the teachings herein to create other embodiments and applications.

BRIEF DESCRIPTION OF THE DRAWINGS

The exact nature of the claimed invention, as well as its objects and advantages, will become readily apparent from consideration of the following specification as illustrated in the accompanying drawings, in which like reference numerals designate like parts, and wherein:

DETAILED DESCRIPTION

The following description is provided to enable any person of ordinary skill in the art to make and use the claimed invention and sets forth the best modes contemplated by the inventors for carrying out the claimed invention. Various modifications, however, will remain readily apparent to those in the art.

Figure 2:
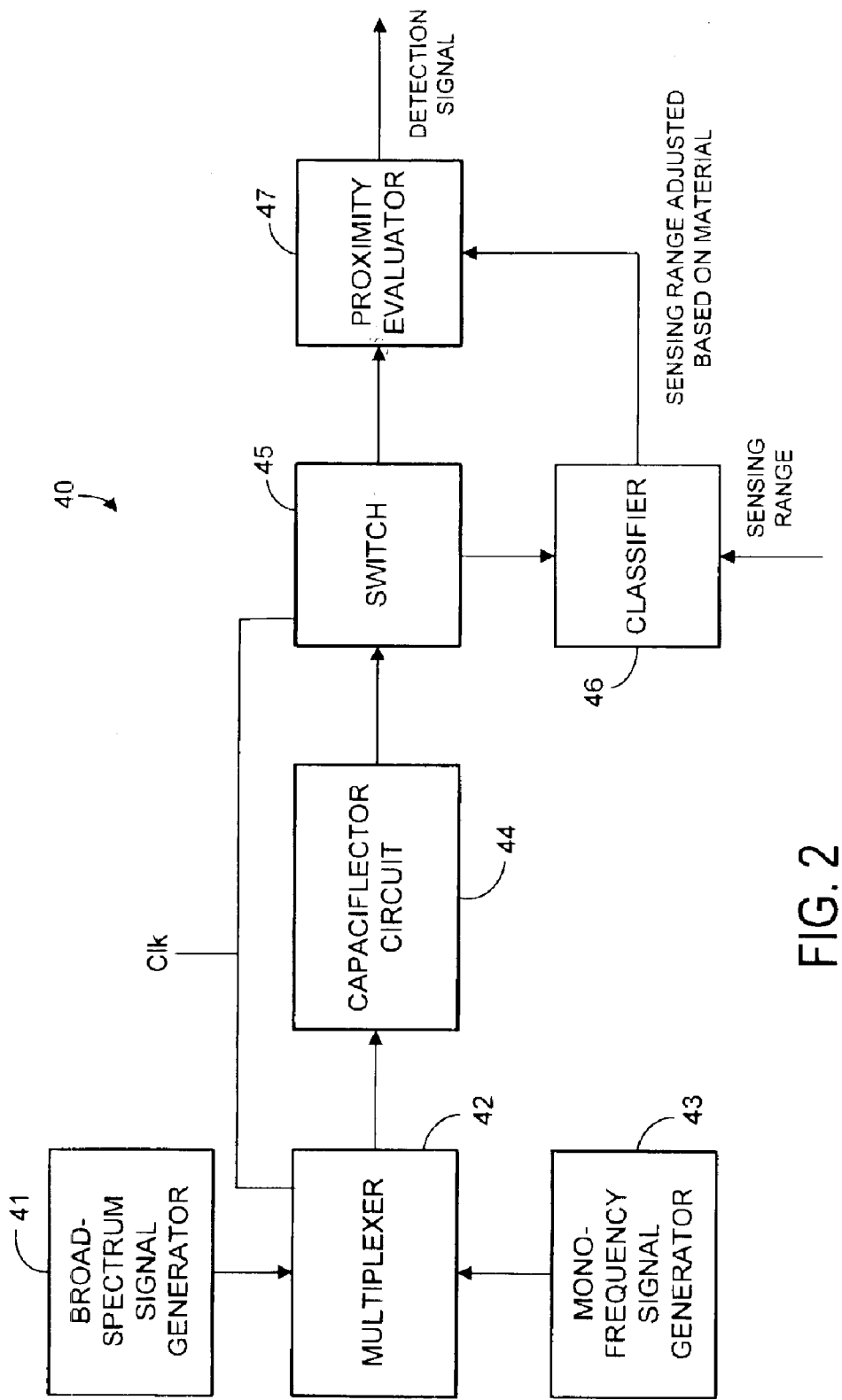
FIG. 2 is a block diagram of an apparatus to provide adaptive proximity sensing according to some embodiments.

FIG. 2 is a block diagram of apparatus 40 according to some embodiments. Apparatus 40 may be used to efficiently and accurately detect an object. Apparatus 40 includes broad-spectrum signal generator 41, multiplexer, 42, monofrequency signal generator 43, capaciflector circuit 44, switch 45, classifier 46 and proximity evaluator 47.

Broad-spectrum signal generator 41 may generate a broad-spectrum input signal. The broad-spectrum input signal may comprise a "chirp" signal as is currently often used for system identification. Broad-spectrum signal generator 41 may therefore comprise a frequency-swept voltage-controlled oscillator. A control voltage of the voltage-controlled oscillator may be swept across a range of voltages to generate a signal having a broad frequency spectrum. Broad-spectrum signal generator 41 may also or alternatively be adapted to generate a white noise signal. The signal generated by generator 41 is received by multiplexer 42.

Multiplexer 42 also receives a signal from mono-frequency signal generator 43. The signal may substantially consist of a single frequency. Accordingly, mono-frequency signal generator 43 may comprise a sine wave generator.

Multiplexer 42 also receives a clock signal Clk. Clock signal Clk is used to select one of the broad-spectrum signal and the substantially mono-frequency signal to transmit to capaciflector circuit 44. More particularly, multiplexer 42 may transmit the broad-spectrum signal to capaciflector circuit 44 in response to a first cycle of clock signal Clk and may transmit the substantially mono-frequency signal to capaciflector circuit 44 in response to a second cycle of clock signal Clk. As will be described in more detail below, clock signal Clk may also be used to determine a processing to be applied to an output signal of capaciflector circuit 44.

Figure 1:
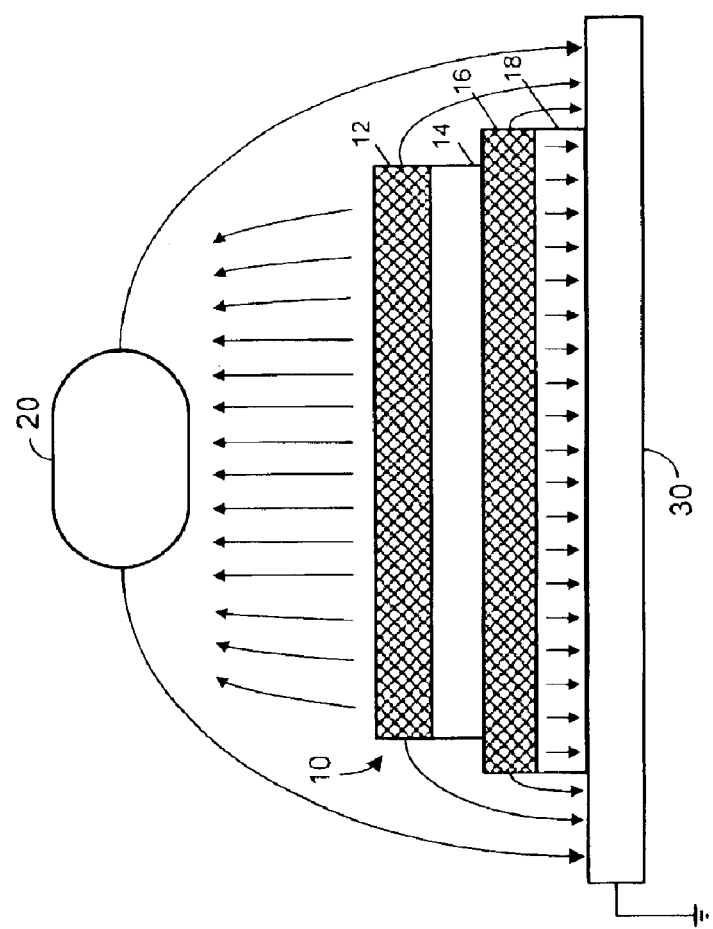
FIG. 1 is block diagram illustrating sensor and shield elements of a capaciflector.

Capaciflector circuit 44 may comprise the arrangement of FIG. 1. More particularly, capaciflector circuit 44 may include sensor element 12 and shield element 16. Particular geometries and compositions of sensor element 12 and shield element 16 may be adapted to a particular use. For example, one or both of sensor element 12 and shield element 16 may comprise a rigid steel plate, a flexible copper strip, and/or a pliable mat of woven conductors. Moreover, any dielectric may be used as dielectrics 14 and 18.

Shield element 16 is capacitively coupled to sensor element 14 and to grounded structure 30. Grounded structure 30 may comprise an exterior housing of an apparatus for which collision detection is desired. In this regard, capaciflector 10 may be applied to a surface of the housing or fully or partially embedded therein.

Capaciflector circuit 44 may comprise a coupling circuit to receive a signal from multiplexer 42, to apply the signal to sensor element 12 and to shield element 16, and to generate an output signal. In some embodiments, the output signal is based on a capacitance between sensor element 12 and object 20. The coupling circuit may comprise a capacitance-based oscillator for detecting the capacitance and for outputting the output signal based on the capacitance, wherein a frequency content of the output signal indicates the capacitance. One coupling circuit suitable for some embodiments is described in U.S. Pat. No. 5,515,001, entitled "Current-measuring Operational Amplifier Circuits".

The output signal is received by switch 45, which outputs the output signal to either classifier 46 or to proximity evaluator 47 based on the clock signal Clk. Continuing with the above example, switch 45 outputs the output signal to classifier 46 in response to the first clock cycle, and outputs the output signal to proximity evaluator 47 in response to the second clock cycle. As a result, an output signal of capaciflector circuit 44 that results from a broad-spectrum input signal is transmitted to classifier 46, while an output signal of capaciflector circuit 44 that results from a substantially mono-frequency input signal is transmitted to proximity evaluator 47.

Classifier 46 determines a material of which object 20 is composed based on a signal output from capaciflector circuit 44. Classifier 46 may comprise any combination of hardware and/or software, including an analog-to-digital converter and a microprocessor. In some embodiments, the output signal received by classifier 46 comprises a permittivity spectrum that represents the material of object 20. Classifier 46 may determine a system response-versus-frequency data set based on the output signal, compare the received data set against several system response-versus-frequency data sets to identify a matching one of the several system response-versus-frequency data sets, and determine a material associated with the matching data set.

Classifier 46 transmits a material-based signal to proximity evaluator 47. In the illustrated embodiment, classifier 46 receives a sensing range signal. The sensing range signal may represent a desired sensing distance. In some embodiments, apparatus 40 is desired to detect objects that are within the desired sensing distance of sensor 10. Classifier 46 may adjust the sensing range signal based on the determined material of object 20. In such a case, the material-based signal transmitted to proximity evaluator 47 is the sensing range signal adjusted based on the determined material.

The adjusted sensing range signal may represent an expected output signal of capaciflector circuit 44 if an object composed of the determined material was positioned at a distance from sensor 10 equal to the desired sensing range, and if the substantially mono-frequency signal of generator 43 was input to capaciflector circuit 44. Classifier 46 may generate this expected output signal based on pre-stored data sets of expected output signals, on a mathematical simulation of capaciflector circuit 44, and/or using other currently or hereafter-known techniques.

Classifier 46 may receive more than one sensing range signal, each of which represents a respective sensing distance. Each of the sensing range signals may be adjusted based on the determined material as described above, and each of the adjusted sensing range signals may be transmitted to proximity evaluator 47.

Proximity evaluator 47 may detect object 20 based on a signal output from capaciflector circuit 44 and on the material-based signal output from classifier 46. Proximity evaluator 47 may also comprise any combination of hardware and/or software. As described above, proximity evaluator 47 may receive the output signal generated by capaciflector circuit 44 in response to a substantially monofrequency input signal.

Proximity evaluator 47 may detect object 20 by comparing the output signal to the material-based signal and by outputting a detection signal based on the comparison. The detection signal may reflect a high logic level if the output signal from capaciflector circuit 44 is greater than the material-based signal, thereby indicating that object 20 and sensor 10 are separated by less than the sensing range. Of course, other conventions may be used in conjunction with some embodiments, such as those in which a low logic level indicates that object 20 is within the sensing range and/or in which the output signal from capaciflector circuit 44 is less than the material-based signal if object 20 and sensor 10 are separated by less than the sensing range.

As mentioned above, proximity evaluator 47 may receive several sensing range signals from classifier 46. Each of these sensing range signals may be compared to the signal output from capaciflector 44 to determine a minimum and maximum distance between object 20 and sensor 10. For example, using the first convention described above, proximity evaluator 47 may determine that a distance between object 20 and sensor 10 is less than a first distance because the output signal from capaciflector circuit 44 is greater than the material-based signal corresponding to the first distance, and may determine that the distance is greater than a second distance because the output signal from capaciflector circuit 44 is less than the material-based signal corresponding to the second distance.

According to some embodiments, the material-based signal transmitted by classifier 46 indicates the material of object 20 but does not specify a sensing range. Proximity evaluator 47 may include elements to detect object 20 based on knowledge of the material and on the output of capaciflector circuit 44 in response to a substantially monofrequency signal. In some embodiments, proximity evaluator 47 receives an indication of the material via the material-based signal and receives a sensing range signal. Proximity evaluator 47 may therefore generate an expected output signal as described above and compare the expected output signal to an output signal of circuit 44. Proximity evaluator 47 may also determine a distance between sensor 10 and object 20 based on the material-based signal and on the signal output by capaciflector circuit 44.

Figure 3:
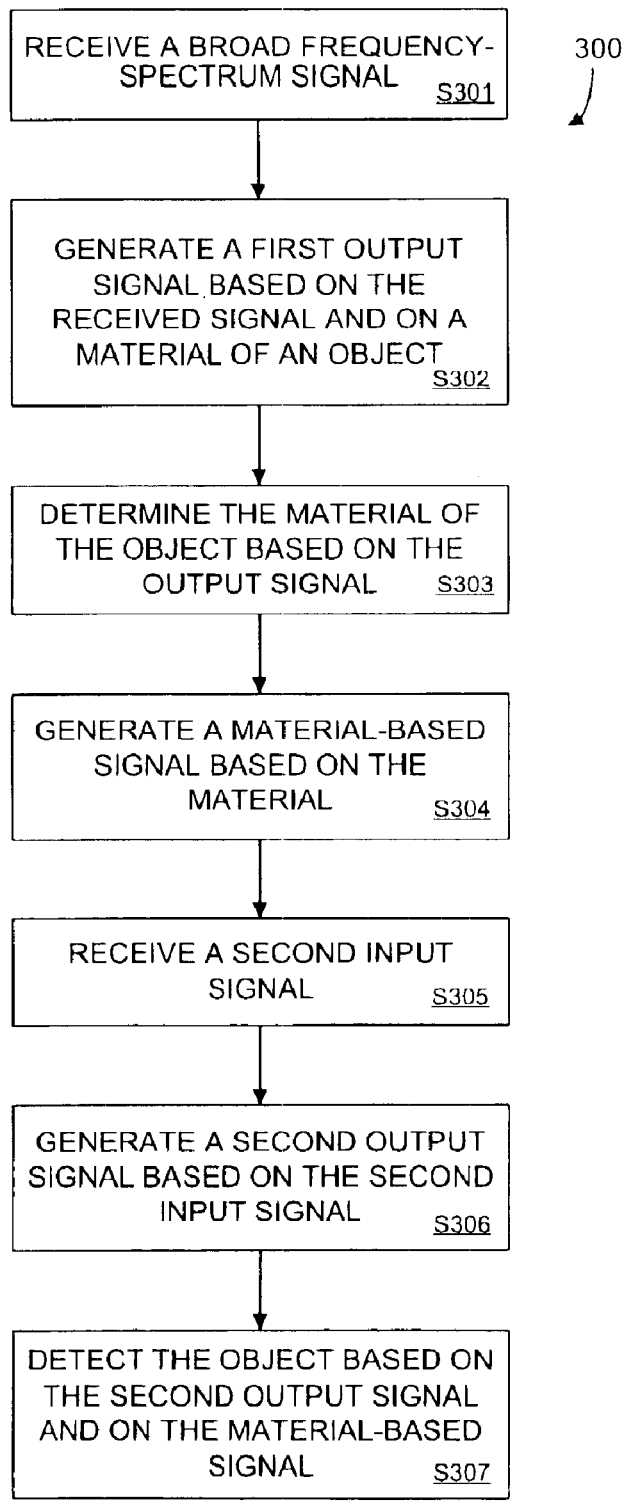
FIG. 3 is a flow diagram of process steps to provide adaptive proximity sensing according to some embodiments.

FIG. 3 is a flow diagram of process steps 300 according to some embodiments. Process steps 300 may be stored in one or more memory devices and executed by one or more processors. One or more process steps 300 may be implemented in hardware and/or may be performed manually.

Capaciflector circuit 44 receives a broad frequency-spectrum signal in step S301. The signal may be a "chirp" signal, a white-noise signal, or any other broad frequency-spectrum signal. In some embodiments, the signal is generated by broad-spectrum signal generator 41 and received from multiplexer 42. Multiplexer 42 may transmit the broad-spectrum signal in response to a first cycle of clock signal Clk.

Figure 4:
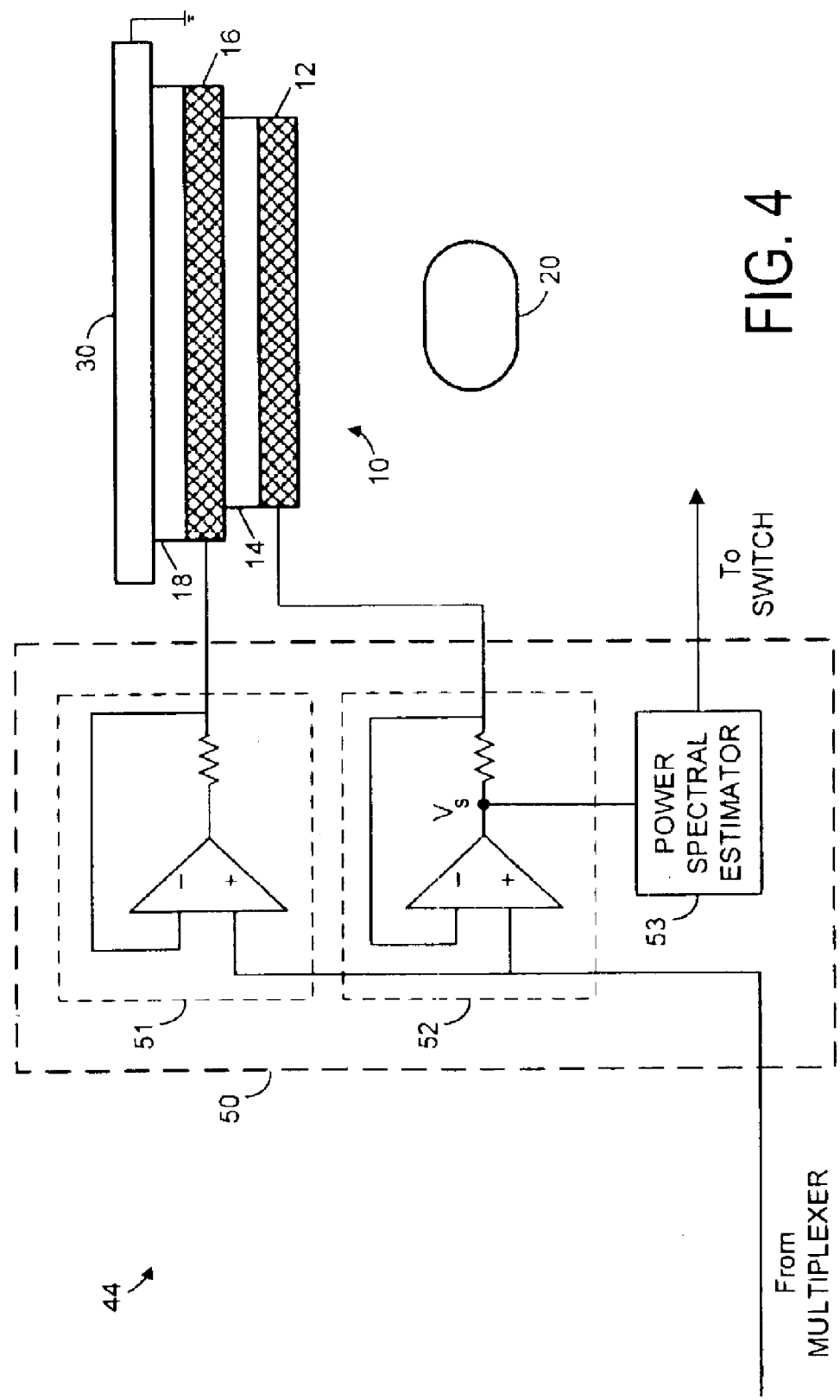
FIG. 4 is a schematic diagram of a capaciflector circuit according to some embodiments.

Next, in step S302, a first output signal is generated based on the broad-spectrum signal and on a material of an object of interest. FIG. 4 illustrates elements that may be used to generate the first output signal in step S302.

As shown, capaciflector circuit 44 includes coupling circuit 50 and capaciflector 10 according to some embodiments. Coupling circuit 50 includes current-measuring voltage follower circuits 51 and 52. Circuits 51 and 52 electrically couple a signal received from multiplexer 42 to sensor element 12 and shield element 16.

As described in above-mentioned U.S. Pat. No. 5,515,001, each of current-measuring voltage follower circuits 51 and 52 includes an operational amplifier (op-amp), a resistor coupled to an output terminal of the op-amp, and a direct feedback connection from the output terminal to a negative input terminal. The input signal received from multiplexer 42 is coupled to a positive input terminal of each op-amp.

The foregoing arrangement effectively locks both sensor element 12 and shield element 16 to the input signal, and to each other. Consequently, the electric field of shield element 16 blocks the ground path of the electric field of sensor element 12. A percentage of the electric field of sensor element 12 that is directed toward object 20 is greater than that of some arrangements lacking shield element 16.

The elements of circuits 51 and 52 generate sensor signal $V_s$, which is proportional to a current through sensor element 12. Signal $V_s$ is received by power spectral estimator 53. Estimator 53 estimates the power spectrum of signal $V_s$ and outputs a signal representing the estimated spectrum. Estimator 53 may comprise a digital signal processor programmed for this purpose. In a case that the broad-spectrum signal is a "chirp" signal, estimator 53 may comprise an AC-to-DC converter.

A material of object 20 is determined in step S303 based on the output signal. In this regard, the first clock cycle not only causes multiplexer 42 to output the broad-spectrum signal but also causes switch 45 to output the output signal to classifier 46. U.S. Pat. No. 5,521,515 describes a method for determining the material based on the output signal that is suitable for some embodiments According to the method, classifier 46 determines a system response-versus-frequency data set based on the output signal. Classifier 46 then determines the material based on the output signal, and more particularly based on the data set. If the data set is plotted, a shape of the resulting curve will be similar to a permittivity-versus-frequency curve that is associated with the material of object 20, if an unknown amplitude factor is ignored. Accordingly, classifier 46 may store and/or have access to several permittivity-versus-frequency data sets that are associated with different materials. Classifier 46 compares the data set with the permittivity-versus-frequency data sets and identifies a matching one of the permittivity-versus-frequency data sets. The material that is associated with the matching permittivity-versus-frequency data set is determined to be the material of object 20. Embodiments are not limited to the foregoing method of step S303.

Classifier 46 generates a material-based signal based on the material in step S304. The material-based signal may simply indicate the determined material. In some embodiments, the material-based signal is based on the determined material and on a sensing range signal received by classifier 46. The material-based signal may represent a signal that is expected to be output by capaciflector circuit 44 if an object composed of the determined material is separated from sensor 10 by the sensing range and if the substantially mono-frequency signal generated by generator 43 is input to capaciflector circuit 44.

A second input signal is then received in step S305. The second input signal may be a substantially mono-frequency signal generated by mono-frequency signal generator 43. More particularly, multiplexer 42 may transmit the substantially mono-frequency signal to capaciflector circuit 44 in response to a second cycle of clock signal Clk.

Capaciflector circuit 44 may generally operate as described above to generate a second output signal based on the second input signal in step S306. Switch 45 transmits the output signal to proximity evaluator 47 in response to the second cycle of clock signal Clk, and proximity evaluator 47 detects object 20 in step S307. Proximity evaluator 47 detects object 20 based on the output signal and on the material-based signal received from classifier 46. Detection of object 20 may include detecting that object 20 is not proximate to sensor 10. Since the detection is based on a determination of the composition of object 20, the detection may be more accurate than that determined by prior systems.

Flow may return to step S301 from step S307 to confirm the material of and to re-detect object 20 and/or to determine the material of and detect any other objects proximate to sensor 10. In some embodiments, flow returns to step S305 from step S307 to re-detect object 20 without re-determining its material.

Figure 5:
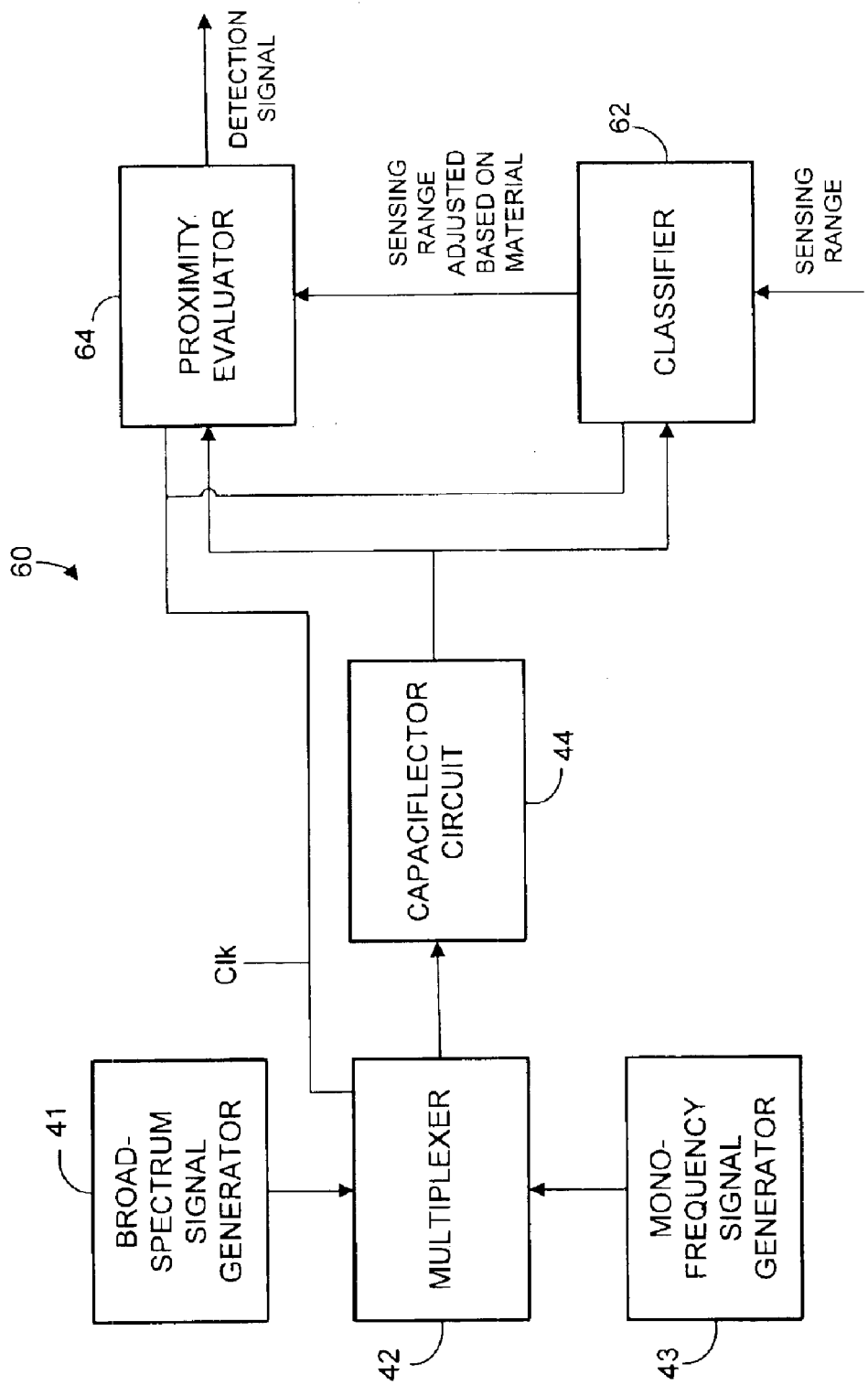
FIG. 5 is a block diagram of an apparatus to provide adaptive proximity sensing according to some embodiments.

FIG. 5 is a block diagram of apparatus 60 according to some embodiments. The elements of apparatus 60 may be identical to similarly-numbered elements of apparatus 40.

Apparatus 60 lacks switch 45 of apparatus 40. Rather, the clock signal Clk is received by classifier 62 and proximity evaluator 64. Classifier 62 and proximity evaluator 64 also both directly receive the output signal of capaciflector circuit 44.

Classifier 62 may perform steps S303 and S304 in response to the first cycle of clock signal CLK. Conversely, proximity evaluator 64 may perform step S307 in response to the second cycle of clock signal Clk. All of the above-discussed variations and functions of a classifier and a proximity evaluator 64 may be implemented in apparatus 60.

Figure 6:
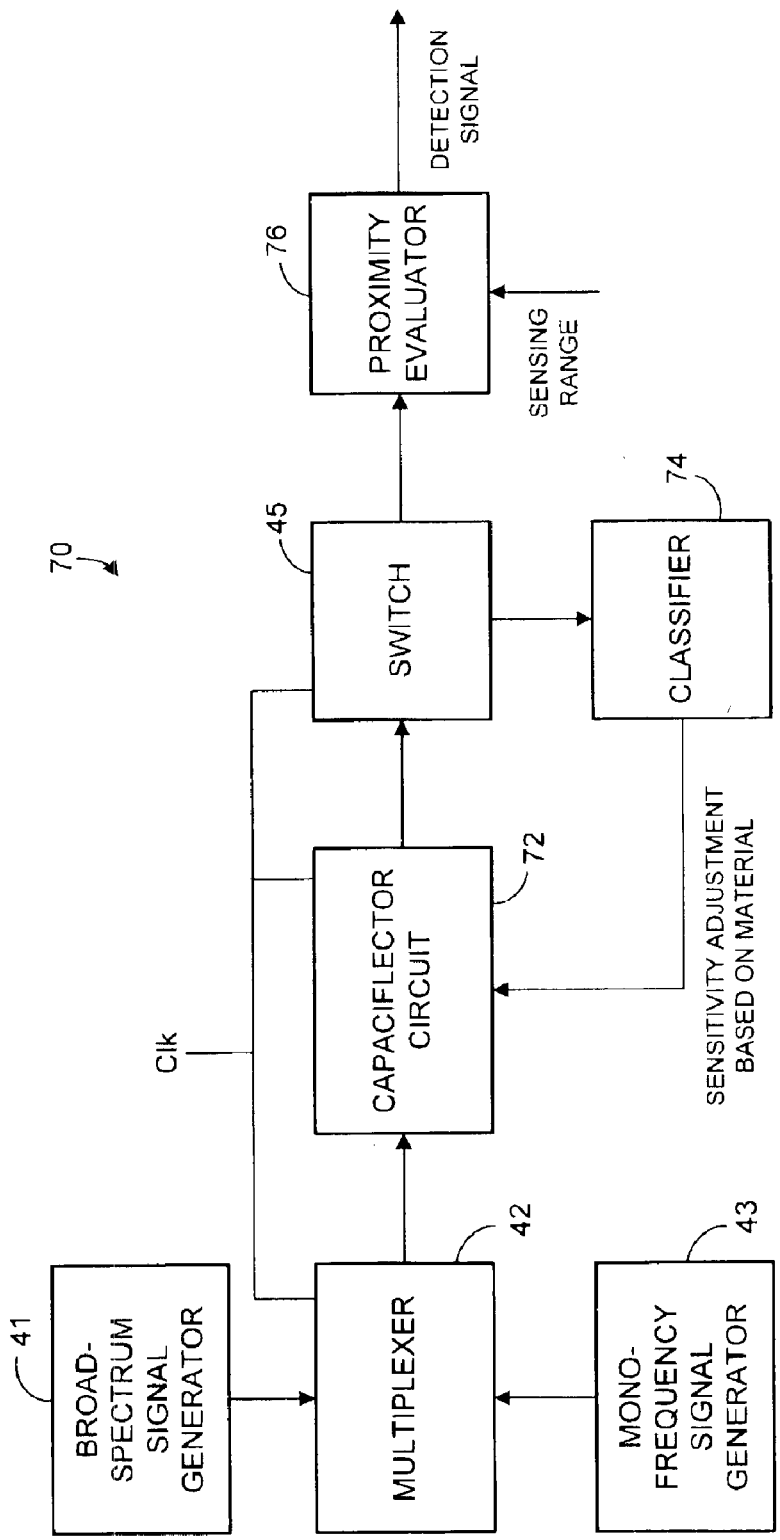
FIG. 6 is a block diagram of an apparatus to provide adaptive proximity sensing according to some embodiments.

FIG. 6 is a block diagram of apparatus 70 according to some embodiments. The elements of apparatus 70 may be identical to similarly-numbered elements of apparatus 40 and apparatus 60. As shown, apparatus 70 is laid out similarly to apparatus 40 but differs in that classifier 74 transmits a material-based signal to capaciflector circuit 72 rather than to proximity evaluator 76, and in that proximity evaluator 76 receives a sensing range signal.

The material-based signal may comprise a sensitivity adjustment signal based on a determined material, a signal merely indicating a material type, and/or a control signal. In either case, capaciflector circuit 72 is adjustable based on the received material-based signal.

Capaciflector circuit 72 may be adjusted to change its sensitivity based on the material-based signal. For example, a sensitivity of capaciflector circuit 72 may be initially set to optimally detect objects of a particular material having a particular permittivity. The sensitivity of capaciflector circuit 72 may be decreased if object 20 is determined to be composed of a material having a permittivity that is less than the particular permittivity.

In some embodiments, the sensitivity of circuit 72 is adjusted by scaling its output signal. Specifically, the signal output from estimator 53 may be received by a voltage follower coupled to a voltage divider. The voltage divider may include a variable resistance that is varied based on the material-based signal so as to scale the received signal in accordance with the determined material. Capaciflector circuit 72 receives clock signal clk to ensure that the above-described components scale the output signal when the input signal is a mono-frequency signal. Many other systems for adjusting capaciflector circuit 72 based on the material-based signal may be used in conjunction with some embodiments.

Apparatus 70 may perform a process similar to process 300. In some embodiments, the process differs in that the first output signal is generated in step S302 using a first configuration of capaciflector circuit 72 and that the first configuration is changed to a second configuration based on the determined material prior to step S306. In this regard, the second output signal is generated using the second configuration in step S306.

Proximity evaluator 76 detects object 20 in step S307 based on the second output signal. Since the second output signal is substantially material-independent, proximity evaluator 76 may apply a same analysis to the second output signal to detect object 20 regardless of the material of which object 20 is composed. The analysis may comprise comparing the second output signal to the received sensing range signal as described above with respect to FIG. 2 and proximity evaluator 47.

Figure 7:
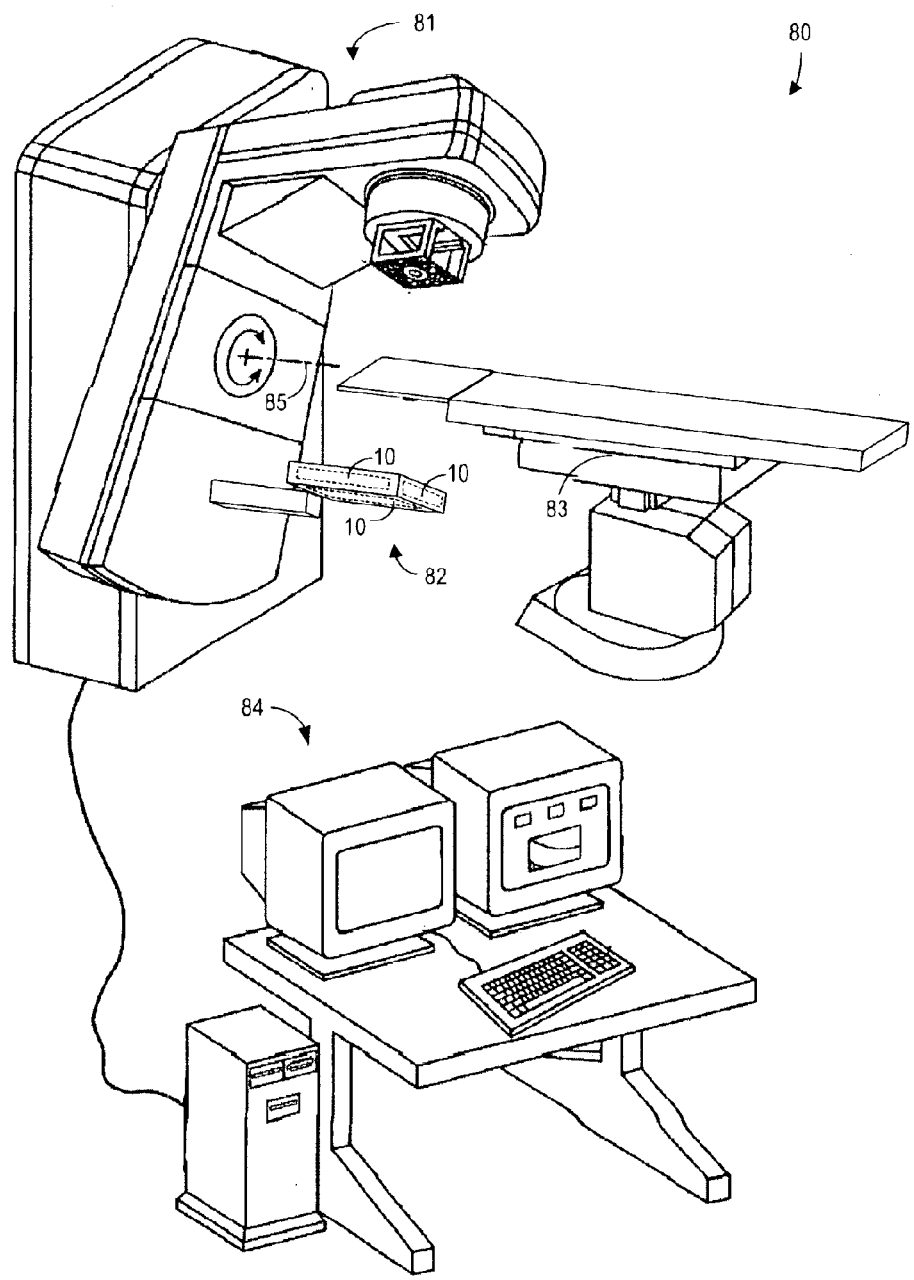
FIG. 7 is a diagram illustrating a radiation therapy room according to some embodiments.

FIG. 7 illustrates radiation therapy room 80 pursuant to some embodiments. Radiation therapy room 80 includes linear accelerator (linac) 81, imaging device 82, table 83, and operator station 84. The elements of radiation therapy room 80 are primarily used to deliver therapeutic radiation to a patient according to a radiation therapy plan.

Linac 81 generates and emits the therapeutic radiation and is rotatable around axis 85. Imaging device 82 acquires images that are used for verification and recordation of a patient position, a radiation field, and an internal patient portal to which radiation is delivered. Table 83 supports a patient during radiation therapy. Table 83 is adjustable to ensure that a therapy area of the patient is properly positioned. Operator station 84 is typically operated by an operator who administers actual delivery of radiation therapy as prescribed by an oncologist.

Capaciflectors 10 are shown embedded on three sides of imaging device 82. In some embodiments, capaciflectors 10 are embedded in each of six sides of imaging device 82. Capaciflectors 10 are intended to sense objects proximate to imaging device 82. More particularly, capaciflectors 10 may be used to determine materials of which the objects are composed and distances from imaging device 82 to the objects. Such determinations may be useful for avoiding collisions that would otherwise result due to the independent movement of linac 81, imaging device 82, table 83, and a patient positioned on table 83.

Capaciflectors 10 of FIG. 7 may be coupled to other elements to implement some embodiments such as apparatus 40, apparatus 60 and apparatus 70. These other elements may be located in imaging device 82, linac 81, operator station 84, and/or in another device. Of course, any of the above-described embodiments may be used to detect objects proximate to any grounded structure.

Generally, those in the art will appreciate that various adaptations and modifications of the above-described embodiments can be configured without departing from the scope and spirit of the claimed invention. Therefore, it is to be understood that, within the scope of the appended claims, embodiments of the invention may be practiced other than as specifically described herein.

What is claimed is:

1. An apparatus comprising:

a sensor element;

a shield element capacitively coupled to the sensor element and to ground;

a coupling circuit to receive an input signal, to electrically couple the received input signal to the sensor element and to the shield element, and to generate a first output signal and a second output signal, the first output signal and the second output signal based on a capacitance between the sensor element and an object;

a classifier to determine a material based on the first output signal, and to output a material-based signal, the material-based signal based on the determined material; and a proximity evaluator to detect the object based on the second output signal and on the material-based signal.

2. An apparatus according to claim 1, wherein the coupling circuit comprises:

one or more signal-generating elements to generate a sensor signal that is proportional to a current through the sensor element.

3. An apparatus according to claim 1, wherein the coupling circuit comprises:

an oscillator to output the first output signal and the second output signal based on the capacitance, wherein a frequency content of the first output signal and the second output signal is to indicate the capacitance.

4. An apparatus according to claim 1, the classifier to determine a system response-versus-frequency data set based on the first output signal, to compare the system response-versus-frequency data set against a plurality of system response-versus-frequency data sets, to identify a matching one of the plurality of system response-versus-frequency data sets based on the comparison, and to determine that the material is associated with the matching one of the plurality of system response-versus-frequency data sets.

5. An apparatus according to claim 4, further comprising:

a broad-spectrum signal generator to generate a broad-spectrum signal;

a signal generator to generate a substantially mono-frequency signal;

a multiplexer to receive the broad-spectrum signal, the substantially mono-frequency signal, and a clock signal, and to selectively transmit one of the broad-spectrum signal and the substantially mono-frequency signal to the coupling circuit based on the clock signal; and a switch to receive the clock signal, and to selectively output the first output signal to the classifier or the second output signal to the proximity evaluator based on the clock signal.

6. An apparatus according to claim 1, further comprising:

a broad-spectrum signal generator to generate a broad-spectrum signal;

a signal generator to generate a substantially mono-frequency signal;

a multiplexer to receive the broad-spectrum signal, the substantially mono-frequency signal, and a clock signal, to transmit the broad-spectrum signal to the coupling circuit in response to a first cycle of the clock signal, and to transmit the mono-frequency signal to the coupling circuit in response to a second cycle of the clock signal; and a switch to receive the clock signal, to output the first output signal to the classifier in response to the first clock cycle, and to output the second output signal to the proximity evaluator in response to the second clock cycle.

7. An apparatus according to claim 1, the classifier to receive a sensing range signal, wherein the material-based signal is based on the sensing range signal.

8. An apparatus according to claim 1, the proximity evaluator to receive a sensing range signal and to detect the object based on the material-based signal and on the sensing range signal.

9. An apparatus according to claim 1, the proximity evaluator to determine a distance between the sensor and the object based on the second output signal and the material-based signal.

10. An apparatus according to claim 1, further comprising:

a broad-spectrum signal generator to generate a broad-spectrum signal;

a signal generator to generate a substantially mono-frequency signal; and a multiplexer to receive the broad-spectrum signal, the substantially mono-frequency signal, and a clock signal, to transmit the broad-spectrum signal to the coupling circuit in response to a first cycle of the clock signal, and to transmit the mono-frequency signal to the coupling circuit in response to a second cycle of the clock signal, wherein the classifier is to receive the clock signal and to output the material-based signal in response to the first cycle of the clock signal, and wherein the proximity evaluator is to receive the clock signal and to detect the object in response to the second cycle of the clock signal.

11. An apparatus comprising:

a sensor element;

a shield element capacitively coupled to the sensor element and to ground;

a coupling circuit to receive an input signal, to electrically couple the received input signal to the sensor element and to the shield element, and to generate a first output signal and a second output signal, the first output signal and the second output signal based on a capacitance between the sensor element and an object; and a classifier to determine a material based on the output signal, and to transmit a material-based signal to the coupling circuit, the material-based signal based on the determined material;

wherein the coupling circuit is adjustable based on the material-based signal.

12. An apparatus according to claim 11, wherein the coupling circuit comprises:

one or more signal-generating elements to generate a sensor signal that is proportional to a current through the sensor element.

13. An apparatus according to claim 11, wherein the coupling circuit comprises:

an oscillator to output the output signal based on the capacitance, wherein a frequency content of the output signal is to indicate the capacitance.

14. An apparatus according to claim 11, the classifier to determine a system response-versus-frequency data set based on the first output signal, to compare the system response-versus-frequency data set against a plurality of system response-versus-frequency data sets, to identify a matching one of the plurality of system response-versus-frequency data sets based on the comparison, and to determine that the material is associated with the matching one of the plurality of system response-versus-frequency data sets.

15. An apparatus according to claim 11, further comprising:

a broad-spectrum signal generator to generate a broad-spectrum signal;

a signal generator to generate a substantially mono-frequency signal;

a multiplexer to receive the broad-spectrum signal, the substantially mono-frequency signal, and a clock signal, to transmit the broad-spectrum signal to the coupling circuit in response to a first cycle of the clock signal, and to transmit the mono-frequency signal to the coupling circuit in response to a second cycle of the clock signal;

a switch to receive the clock signal, to output the first output signal to the classifier in response to the first clock cycle; and a proximity evaluator to detect the object based on the second output signal, wherein the switch is to output the second output signal to the proximity evaluator in response to the second clock cycle.

16. An apparatus according to claim 15, the proximity evaluator to receive a sensing range signal and to detect the object based on the second output signal and on the sensing range signal.

17. An apparatus according to claim 15, the proximity evaluator to determine a distance between the sensor and the object.

18. An apparatus according to claim 11, the classifier to receive a sensing range signal, wherein the material-based signal is based on the sensing range signal and on the determined material.

* * * * *